United States Patent
McClendon et al.

(10) Patent No.: US 11,517,648 B2
(45) Date of Patent: Dec. 6, 2022

(54) NANOFIBER PASTE FOR GROWTH FACTOR DELIVERY AND BONE REGENERATION

(71) Applicant: Northwestern University, Evanston, IL (US)

(72) Inventors: Mark Trosper McClendon, Chicago, IL (US); Samuel I. Stupp, Chicago, IL (US); Sungsoo Lee, Chicago, IL (US); Erin L. Hsu, Glenview, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/293,666

(22) Filed: Oct. 14, 2016

(65) Prior Publication Data

US 2017/0106120 A1    Apr. 20, 2017

Related U.S. Application Data

(60) Provisional application No. 62/241,410, filed on Oct. 14, 2015.

(51) Int. Cl.
| | | |
|---|---|---|
| *A61K 38/18* | (2006.01) | |
| *A61L 27/54* | (2006.01) | |
| *A61L 27/48* | (2006.01) | |
| *A61L 27/52* | (2006.01) | |

(52) U.S. Cl.
CPC .......... *A61L 27/54* (2013.01); *A61K 38/1875* (2013.01); *A61L 27/48* (2013.01); *A61L 27/52* (2013.01); *A61L 2300/414* (2013.01); *A61L 2400/06* (2013.01); *A61L 2400/12* (2013.01); *A61L 2430/02* (2013.01); *A61L 2430/06* (2013.01); *A61L 2430/34* (2013.01)

(58) Field of Classification Search
CPC ..... A61K 38/39; A61K 38/1875; A61L 27/24; A61L 27/56; A61L 27/58
See application file for complete search history.

(56) References Cited

U.S. PATENT DOCUMENTS

| | | | |
|---|---|---|---|
| 4,412,947 A * | 11/1983 | Cioca | A61K 9/70 106/150.1 |
| 5,679,723 A * | 10/1997 | Cooper | A61L 27/32 424/426 |
| 7,030,167 B2 | 4/2006 | Gunther | |
| 7,371,719 B2 | 5/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,076,295 B2 | 12/2011 | Hulvat et al. | |
| 8,080,262 B2 | 12/2011 | Stupp et al. | |
| 8,114,834 B2 | 2/2012 | Stupp et al. | |
| 8,114,835 B2 | 2/2012 | Stupp et al. | |
| 8,124,583 B2 | 2/2012 | Stupp et al. | |
| 8,138,140 B2 | 3/2012 | Stupp et al. | |
| 8,236,800 B2 | 8/2012 | Degrado et al. | |
| 8,450,271 B2 | 5/2013 | Shah et al. | |
| 8,512,693 B2 | 8/2013 | Capito et al. | |
| 8,546,338 B2 | 10/2013 | Donners et al. | |
| 8,580,923 B2 | 11/2013 | Stupp et al. | |
| 8,658,763 B2 | 2/2014 | Rapaport | |
| 8,735,354 B2 | 5/2014 | Jun et al. | |
| 8,748,569 B2 | 6/2014 | Stupp et al. | |
| 8,772,228 B2 | 7/2014 | Stupp et al. | |
| 8,940,858 B2 | 1/2015 | Stupp et al. | |
| 8,968,417 B2 | 3/2015 | Chachques et al. | |
| 9,011,914 B2 | 4/2015 | Wong Po Foo et al. | |
| 9,040,626 B2 | 5/2015 | Chien et al. | |
| 9,044,514 B2 | 6/2015 | Xu et al. | |
| 9,169,294 B2 | 10/2015 | Zha et al. | |
| 9,512,404 B2 | 12/2016 | Stupp et al. | |
| 9,556,232 B2 | 1/2017 | Zha et al. | |
| 2004/0001893 A1 * | 1/2004 | Stupp | C07K 14/78 424/488 |

(Continued)

FOREIGN PATENT DOCUMENTS

| | | | | |
|---|---|---|---|---|
| CA | | 2663642 A1 * | 10/2009 | ............. A61P 43/00 |
| JP | | 2009-539839 | 11/2009 | |

(Continued)

OTHER PUBLICATIONS

Furth (Chapter 6—Tissue Engineering: Future Perspectives in Principles of Tissue Engineering (Fourth Edition) 2014, pp. 83-123, Available online Oct. 31, 2013, of record) (Year: 2013).*
Vo (Strategies for Controlled Delivery of Growth Factors and Cells for Bone Regeneration, Adv Drug Deliv Rev. 2012; 64(12): 1292-1309, of record) (Year: 2012).*
Baba et al. "Efficacy of bone regeneration using collagen microspheres as scaffold", J Osaka Dent Univ, 2008, pp. 9-15 (Year: 2008).*
Lee et al. "Bone regeneration with low dose BMP-2 amplified by biomimetic supramolecular nanofibers with collagen scaffolds", Biomaterials, 2013, pp. 452-459 (Year: 2013).*

(Continued)

*Primary Examiner* — Lianko G Garyu
(74) *Attorney, Agent, or Firm* — Casimir Jones SC; David W. Staple

(57) ABSTRACT

Provided herein are compositions comprising a composite of peptide amphiphiles and biocompatible particles and methods of use thereof for treatment of bone and/or tissue defects. In particular, compositions comprise a slurry paste of a peptide amphiphile nanofiber solution mixed with solid biocompatible particles, and find use in tissue/bone regeneration, growth factor delivery, and/or cell delivery.

7 Claims, 7 Drawing Sheets

Specification includes a Sequence Listing.

(56) References Cited

U.S. PATENT DOCUMENTS

| | | | |
|---|---|---|---|
| 2006/0084607 A1 | 4/2006 | Spirio et al. | |
| 2006/0145934 A1 | 7/2006 | Park et al. | |
| 2006/0222680 A1* | 10/2006 | Yang | B01J 13/14 |
| | | | 424/426 |
| 2010/0297096 A1* | 11/2010 | Rapaport | A61K 38/03 |
| | | | 424/94.1 |
| 2012/0264912 A1 | 10/2012 | Stupp et al. | |
| 2013/0101628 A1 | 4/2013 | Webber et al. | |
| 2013/0116789 A1 | 5/2013 | Chachques et al. | |
| 2013/0281547 A1 | 10/2013 | Spirio et al. | |
| 2014/0219981 A1 | 8/2014 | Rapaport | |
| 2015/0093574 A1 | 4/2015 | Tayi et al. | |
| 2016/0159869 A1 | 6/2016 | Stupp et al. | |
| 2017/0021056 A1 | 1/2017 | Stupp et al. | |

FOREIGN PATENT DOCUMENTS

| | | | | |
|---|---|---|---|---|
| WO | WO 2007/145909 | | 12/2007 | |
| WO | WO 2008/101104 | | 8/2008 | |
| WO | WO-2009042514 A1 * | 4/2009 | | A61L 27/56 |
| WO | WO 2010/120830 | | 10/2010 | |
| WO | WO 2012/149515 | | 11/2012 | |
| WO | WO 2003/084980 | | 10/2013 | |
| WO | WO 2014/104981 | | 7/2014 | |
| WO | WO 2014/133027 | | 9/2014 | |
| WO | WO 2015/048746 | | 4/2015 | |
| WO | WO 2016/149363 | | 9/2016 | |
| WO | WO 2017/066545 | | 4/2017 | |

OTHER PUBLICATIONS

Rossi et al. "Polymeric scaffolds as stem cell carriers in bone repair", J Tissue Eng Regen Med, 2013 (Year: 2013).*

Lissenberg-Thunnissen et al. "Use and efficacy of bone morphogenetic proteins in fracture healing", International Orthopaedics, 2011, pp. 1271-1280 (Year: 2011).*

Milijkovic et al. "Review: Chondrogenesis, bone morphogenetic protein-4 and mesenchymal stem cells", Osteoarthritis and Cartilage, 2008, pp. 1121-1130 (Year: 2008).*

Lee et al. "Gel Scaffolds of BMP-2-Binidng Peptide Amphiphile Nanofibers for Spinal Arthrodesis", Adv. Healthcare Mater. 2015, 4, 131-141 (Year: 2015).*

Bowers et al., Risk factors and rates of bone flap resorption in pediatric patients after decompressive craniectomy for traumatic brain injury. J Neurosurg Pediatr. May 2013;11(5):526-32.

Dunisch et al., Risk factors of aseptic bone resorption: a study after autologous bone flap reinsertion due to decompressive craniotomy. J Neurosurg. May 2013;118(5):1141-7.

Lee et al., Bone regeneration with low dose BMP-2 amplified by biomimetic supramolecular nanofibers within collagen scaffolds. Biomaterials. Jan. 2013;34(2):452-9.

Lee et al., Gel scaffolds of BMP-2-binding peptide amphiphile nanofibers for spinal arthrodesis. Adv Healthc Mater. Jan. 7, 2015;4(1):131-41.

Matson et al., Peptide Self-Assembly for Crafting Functional Biological Materials. Curr Opin Solid State Mater Sci. Dec. 2011;15(6):225-235.

Shah et al., Supramolecular design of self-assembling nanofibers for cartilage regeneration. Proc Natl Acad Sci U S A. Feb. 23, 2010;107(8):3293-8.

Stevens et al., Exploring and engineering the cell surface interface. Science. Nov. 18, 2005;310(5751):1135-8.

Webber et al., Reprint of: Development of bioactive peptide amphiphiles for therapeutic cell delivery. Acta Biomater. Sep. 2015;23 Suppl:S42-51.

International Search Report and Written Opinion for PCT/US2016/057007, dated Dec. 29, 2016, 8 pages.

Hosseinkhani et al., Bone regeneration on a collagen sponge self-assembled peptide-amphiphile nanofiber hybrid scaffold. Tissue Eng. Jan. 2007;13(1):11-9.

Extended European Search Report for EP16856259.3 dated May 14, 2019, 9 pages.

* cited by examiner

| | Collagen | PA Nanofibers | rhBMP-2 conc. | rhBMP-2 per animal | Volume per side(mL) |
|---|---|---|---|---|---|
| Group 1 | ACS sponge | No | 5ug/mL | 30ug | 3 |
| Group 2 | ACS sponge | No | 10ug/mL | 60ug | 3 |
| Group 3 | ACS sponge | Yes | 5.55ug/mL | 30ug | 2.7 |
| Group 4 | ACS sponge | Yes | 11.1ug/mL | 60ug | 2.7 |
| Group 5 | Collagen Particles | Yes | 7.5ug/mL | 30ug | 2 |
| Group 6 | Collagen Particles | Yes | 15ug/mL | 60ug | 2 |
| Group 7 | Collagen Particles | Yes | 0ug/mL | GF-Free | 2 |

| | Based on Blinded Manual Palpation | | | Treatment | |
|---|---|---|---|---|---|
| Group# | % Fusion | Fusion Score | Std. Dev. | Delivery Vehicle | GF Dose |
| Group 1 | 0 | 0.00 | 0.00 | ACS | 30ug |
| Group 2 | 50 | 1.04 | 1.05 | ACS | 60ug |
| Group 3 | 100 | 2.00 | 0.00 | ACS + Nanofibers | 30ug |
| Group 4 | 100 | 2.00 | 0.00 | ACS + Nanofibers | 60ug |
| Group 5 | 100 | 1.39 | 0.39 | NanoSlurry | 30ug |
| Group 6 | 100 | 2.00 | 0.00 | NanoSlurry | 60ug |
| Group 7 | 33 | 0.50 | 0.84 | NanoSlurry | GF-Free |

Group 1: 30µg BMP-2 on ACS

Group 2: 60µg BMP-2 on ACS

Group 3: 30µg BMP-2 + BMP2-PA

Group 4: 60µg BMP-2 + BMP2-PA

Group 5: 30ug rhBMP-2 + NanoSlurry

Group 6: 60ug rhBMP-2 + NanoSlurry

Group 7: 0ug rhBMP-2 NanoSlurry

|  | Based on Blinded Manual Palpation | | | Treatment | |
| --- | --- | --- | --- | --- | --- |
| Group# | % Fusion | Fusion Score | Std. Dev. | Delivery Vehicle | GF Dose |
| Group 1 | 0 | 0.00 | 0.00 | ACS | 30ug |
| Group 2 | 50 | 1.04 | 1.05 | ACS | 60ug |
| Group 3 | 100 | 2.00 | 0.00 | ACS + Nanofibers | 30ug |
| Group 4 | 100 | 2.00 | 0.00 | ACS + Nanofibers | 60ug |
| Group 5 | 100 | 1.39 | 0.39 | NanoSlurry | 30ug |
| Group 6 | 100 | 2.00 | 0.00 | NanoSlurry | 60ug |
| Group 7 | 33 | 0.50 | 0.84 | NanoSlurry | GF-Free |

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Ala Ala Val Val
1

<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Ala Ala Ala Val Val Val
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic peptide
```

```
<400> SEQUENCE: 3

Val Val Ala Ala
1

<210> SEQ ID NO 4
<211> LENGTH: 7
<212> TYPE: PRT
<213> ORGANISM: Artificial sequence
<220> FEATURE:
<223> OTHER INFORMATION: Synthetic peptide

<400> SEQUENCE: 4

Lys Lys Ala Ala Val Val Lys
1               5

<210> SEQ ID NO 5
<211> LENGTH: 20
<212> TYPE: PRT
<213> ORGANISM: Artificial sequence
<220> FEATURE:
<223> OTHER INFORMATION: Synthetic peptide

<400> SEQUENCE: 5

Thr Ser Pro His Val Pro Tyr Gly Gly Gly Ser Glu Glu Glu Ala Ala
1               5                   10                  15

Ala Val Val Val
            20

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Glu Glu Glu Ala Ala Ala Val Val Val
1               5
```

NANOFIBER PASTE FOR GROWTH FACTOR DELIVERY AND BONE REGENERATION

CROSS REFERENCE TO RELATED APPLICATIONS

The present invention claims the priority benefit of U.S. Provisional Patent Application 62/241,410, filed Oct. 14, 2015, which is incorporated by reference in its entirety.

STATEMENT REGARDING FEDERAL FUNDING

This invention was made with government support under R01 DE015920 awarded by the National Institutes of Health. The government has certain rights in the invention.

FIELD

Provided herein are compositions comprising a composite of peptide amphiphiles and biocompatible particles and methods of use thereof for treatment of bone and/or tissue defects. In particular, compositions comprise a slurry paste of a peptide amphiphile nanofiber solution mixed with solid biocompatible particles, and find use in tissue/bone regeneration, growth factor delivery, and/or cell delivery.

BACKGROUND

Bone resorption and nonunion of the bone defects ((e.g., cranial defect, spinal defects, etc.) are of critical concern (See, e.g., Dünisch, et al. *J. Neurosurg.* 118, 1141-1147 (2013); Bowers et al. *J Neurosurg Pediatr* 11, 526-532 (2013).; herein incorporated by reference in their entireties. Compositions to facilitate bone regeneration and delivery of growth factors are needed.

SUMMARY

Provided herein are compositions comprising a composite of peptide amphiphiles and biocompatible particles and methods of use thereof for treatment of bone and/or tissue defects. In particular, compositions comprise a slurry paste of a peptide amphiphile nanofiber solution mixed with solid biocompatible particles, and find use in tissue/bone regeneration, growth factor delivery, and/or cell delivery.

In some embodiments, provided herein are materials that are useful in the repair of bone/tissue defects. Embodiments herein find use in delivery of growth factors (e.g., localized delivery, delivery of proteins, etc.), use as a bone void filler, and/or in bone regeneration (e.g., bone growth infusion induction for spinal infusion, etc.). In some embodiments, compositions herein comprise slurry pastes made from a peptide nanofiber solution mixed with solid biocompatible particles, such as collagen, cross-linked hyaluronic acid, polylactic glycolic acid (PLGA), and/or other bio-polymer particles. In some embodiments, the paste-like consistency of this mixture allows the material to be adapted (e.g., by a surgeon) into any size bone defect. After implantation, the nanofibers cause the paste to gel in the shape of the bone defect. In some embodiments, materials herein are osteoconductive and osteoinductive, and/or are used to deliver growth factors into defect sites. In some embodiments, growth factors are released over time (e.g., hours, days, weeks) from the nanofiber gels.

DEFINITIONS

Figure 1A:
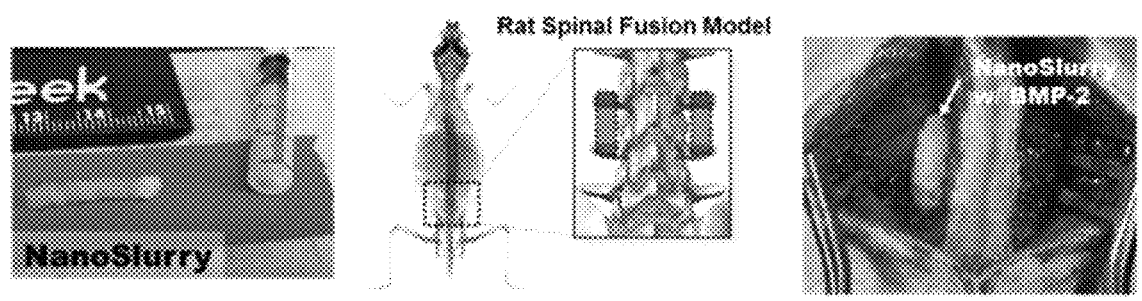
FIGS. 1A-B. (A) Rat spinal fusion model. (B) Fusion scores, measured in 3 experimental groups; group 1: Collagen sponge with 100 ng BMP2, group 2: 100 ng BMP2 with collagen particles, group 3: 100 ng BMP2 with NanoSlurry.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO: Z (e.g., 100 amino acids) may have up to X substitutions (e.g., 10) relative to SEQ ID NO: Z, and may therefore also be expressed as "having X (e.g., 10) or fewer substitutions relative to SEQ ID NO: Z."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both), and optionally a bioactive segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., β-sheet forming); (3) a charged peptide segment, and (4) a bioactive segment (e.g., linker segment).

As used herein and in the appended claims, the term "lipophilic moiety" or "hydrophobic moiety" refers to the moiety (e.g., an acyl, ether, sulfonamide, or phosphodiestermoiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "bioactive peptide" refers to amino acid sequences that mediate the action of sequences, molecules, or supramolecular complexes associated therewith. Peptide amphiphiles and structures (e.g., nanofibers)

bearing bioactive peptides (e.g., a TF-targeting sequence, etc.) exhibits the functionality of the bioactive peptide.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

DETAILED DESCRIPTION

Provided herein are compositions comprising a composite of peptide amphiphiles and biocompatible particles and methods of use thereof for treatment of bone and/or tissue defects. In particular, compositions comprise a slurry paste of a peptide amphiphile nanofiber solution mixed with solid biocompatible particles, and find use in tissue/bone regeneration, growth factor delivery, and/or cell delivery.

Advantages of the present compositions and methods over existing bone void fillers include: (1) the capacity to 'gel' under physiological conditions (e.g., induced by the surrounding naturally occurring ions) to accommodate any shape; (2) delivery of any cocktail of growth factors or other agents that are added to the mixture which become bound to the highly charged nanofiber gel; and/or (3) flexibility to use any biocompatible particles in combination with a diverse array of regenerative peptide amphiphile molecules.

Compositions herein comprise two primary components; (1) biocompatible particles (e.g., collagen particles, hyaluronic acid gel particles, and/or other biopolymer particles), and (2) peptide amphiphile nanofiber solutions (e.g., with or without growth factors). In some embodiments, growth factors (GF) and/or GF-binding peptides are displayed on the peptide amphiphile nanofibers and/or embedded within the compositions or peptide amphiphile nanofiber solutions. In some embodiments, cells (e.g., osteoblasts, stem or other progenitor cells, chondrocytes, etc.) embedded within the compositions or peptide amphiphile nanofiber solutions.

Exemplary compositions described herein use collagen particles, although other suitable biopolymers are within the scope herein. In some embodiments, exemplary collagen particles are prepared from porous collagen sponges prepared with the method of cross-linking freeze drying method described elsewhere. These sponges are cut into small pieces (1 cm×1 cm) dampened with 50 uL of water, then flash frozen with liquid $N_2$, then ground up into a fine powder using a mortar and pestle while in the frozen state. This powderized collagen is lyophilized into a dry powder that is mixed with nanofiber solution. Similar methods find use in the preparation of other polymeric particles using other biocompartible starting materials.

Peptide amphiphile (PA) nanofiber solutions may comprise any suitable combination of PAs. In some embodiments, at least 0.05 mg/mL (e.g., 0.10 mg/ml, 0.15 mg/ml, 0.20 mg/ml, 0.25 mg/ml, 0.30 mg/ml, 0.35 mg/ml, 0.40 mg/ml, 0.45 mg/ml, 0.50 mg/ml, 0.60 mg/ml, 0.70 mg/ml, 0.80 mg/ml, 0.90 mg/ml, 1.0 mg/ml, or more, or ranges therebetween), of the solution is a filler PA (e.g., without a peptide epitope or other nanofiber surface displayed moiety). In some embodiments, at least 0.25 mg/mL of the solution is a filler PA. In some embodiments, a filler PA is a non-bioactive PA molecule having highly charged glutamic acid residues on the terminal end of the molecule (e.g., surface-displayed end). These negatively charged PAs allow for the gelation to take place between nanofibers via ionic crosslinks. The filler PAs provide the ability to incorporate other bio-active PAs molecules into the nanofiber matrix while still ensuring the ability of the nanofibers solution to gel. In some embodiments, the solutions are annealed for increased viscosity and stronger gel mechanics. These filler PAs have sequences are described in, for example, U.S. Pat. No. 8,772,228 (e.g., $V_3A_3E_3$, lauric acid-$V_3A_3E_3$), which is herein incorporated by reference in its entirety.

In an exemplary embodiment, the biocompatible particles and peptide amphiphile nanofiber solution are mixed at 5 wt % biocompatible particles (e.g., collagen particles, hyaluronic acid gel particles, etc.) and 1 wt % PA in neutral pH water. Other ranges (e.g., 1 wt %-20 wt % (e.g., 1, 2, 3, 4, 5, 6, 7, 8, 9 10, 11, 12, 13, 14, 15, 16, 17, 18, 19, 20, or any ranges there between) biocompatible particles; 0.1 wt %-10 wt % (e.g., 0.1, 0.2, 0.3, 0.4, 0.5, 0.6, 0.7, 0.8, 0.9, 1, 2, 3, 4, 5, 6, 7, 8, 9 10, or any ranges there between) PAs) may be employed. In particular embodiments, collagen (or another polymer) is used from 0 wt % to 20 wt %, and the PAs are used at 0.05 wt % to 3 wt %. In some embodiments, growth factors, such as BMP-2, are mixed into the PA solution before combining with the collagen particles but after annealing the PA solution. In some embodiments, cells (e.g., osteoblasts, stem or other progenitor cells, chondrocytes, etc.) are mixed into the PA solution before combining with the collagen particles but after annealing the PA solution. In some embodiments, cells and/or growth factors are added after the particles.

Suitable biocompatible polymers for use as particles in the materials herein are selected from the group consisting of: PLA, PLLA, PGA, PGLA, PCL, chitosan, polylactides, polyglycolides, epsilon-caprolactone, polyhydroxyvaleric acid, polyhydroxybutyric acid, other polyhydroxy acids, polytrimethylene carbonate, polyamines, vinyl polymers, polyacrylic acids and their derivatives containing ester, polyethylene glycols, polydioxanones, polycarbonates, polyacetals, polyorthoesters, polyamino acids, polyphosphoesters, polyesteramides, polyfumerates, polyanhydrides, polycyanoacrylates, polyoxamers, polyurethanes, polyphosphazenes, aliphatic polyesters, poly(amino acid), copoly (ether-ester), polyakylene oxalate, polyamides, poly(iminocarbonate), polyoxaester, polyamidoesters, amine group-containing polyoxaester, polyacetal, polyalkanoate, gelatin, collagen, elastine, polysaccharide, alginate, chitin, hyaluronic acid, and combinations thereof. Methods described herein and/or understood in the field find use in preparing particles of the above-listed biocompatible polymers.

In some embodiments, particles are of any suitable size and shape. In some embodiments, particles are microparticles and have mean diameters of between 1 μm and 1 mm (e.g., 1 μm, 2 μm, 5 μm, 10 μm, 20 μm, 30 μm, 40 μm, 50 μm, 60 μm, 70 μm, 80 μm, 90 μm, 1 mm, or ranges therebetween). In some embodiments, particles are nanoparticles and have mean diameters of between 1 nm and 1 μm (e.g., 1 nm, 2 nm, 5 nm, 10 nm, 20 nm, 30 nm, 40 nm, 50 nm, 60 nm, 70 nm, 80 nm, 90 nm, 1 nm, or ranges therebetween). In some embodiments, particles are generated using any suitable techniques, such as, freezing (e.g., under liquid $N_2$), drying, freeze drying, lyophilizing, grinding, milling, exposure to solvent (e.g., ethanol), sieving, and combinations thereof.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH2, and —NH2.

In some embodiments, peptide amphiphiles comprise a hydrophobic (non-peptide) segment linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules self-assemble (e.g., into cylindrical micelles (a.k.a nanofibers)) that bury the lipophilic segment in their core and display the bioactive peptide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 1), AAAVVV (SEQ ID NO: 2), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of CH2, O, $(CH_2)_2O$, $O(CH_2)_2$, NH, and C=O groups (e.g., CH2(O $(CH_2)_2)_2$NH, CH2$(O(CH_2)_2)_2$NHCO$(CH_2)_2$CCH, etc.). In some embodiments, a spacer or linker further comprises additional bioactive groups, substituents, branches, etc.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, bioactive segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural segment (e.g., comprising VVAA; SEQ ID NO: 3); and (c) a charged segment (e.g., comprising KK, EE, etc). In some embodiments, any PAs within the scope described herein, comprising the components described herein, or within the skill of one in the field, may find use herein.

In some embodiments, peptide amphiphiles comprise a bioactive moiety. In particular embodiments, a bioactive moiety is the C-terminal or N-terminal most segment of the PA. In some embodiments, the bioactive moiety is attached to the end of the charged segment. In some embodiments, the bioactive moiety is exposed on the surface of an assembled PA structure (e.g., nanofiber). A bioactive moiety is typically a peptide (e.g., growth factor, etc.), but is not limited thereto. In some embodiments, a bioactive moiety is a peptide sequence that binds a peptide or polypeptide of interests, for example, a growth factor. Bioactive peptides and other moieties for achieving functionality will be understood. In some embodiments, bioactive moieties are provided having binding affinity for a target protein (e.g., growth factor). The binding affinity ($K_d$) may be chosen from one of: less than 10 µM, less than 1 µM, less than 100 nM, less than 10 nM, less than 1 nM, less than 100 µM. In some embodiments, bioactive moieties are provided having at least 70% (e.g., 70%, 75%, 80%, 85%, 90%, 95%, 98%, 99%, or ranges therebetween) sequence identity with all or an active portion of a growth factor.

In some embodiments, a peptide amphiphile comprises: (a) a hydrophobic tail comprising an alkyl chain of 8-24 carbons; (b) a structural segment (e.g., comprising VVAA (SEQ ID NO: 3), AAVV (SEQ ID NO: 1), VA, AV, etc.); (c) a charged segment (e.g., comprising KK, EE, EK, KE, etc.), and a bioactive peptide (e.g., growth factor or GF-targeting peptide). In some embodiments, a PA further comprises an attachment segment or residue (e.g., K) for attachment of the hydrophobic tail to the peptide portion of the PA. In some embodiments, the hydrophobic tail is attached to a lysine side chain.

In some embodiments, a peptide amphiphile comprises (e.g., from C-terminus to N-terminus or from N-terminus to C-terminus): bioactive peptide (e.g., growth factor or GF-targeting peptide)-charged segment (e.g., comprising KK, EE, EK, KE, etc.)-structural segment (e.g., comprising VVAA (SEQ ID NO: 3), AAVV (SEQ ID NO: 1), VA, AV, etc.)-hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., growth factor or GF-targeting peptide)-charged segment (e.g., comprising KK, EE, EK, KE, etc.)-structural segment (e.g., comprising VVAA (SEQ ID NO: 3), AAVV (SEQ ID NO: 1), VA, AV, etc.)-attachment segment or peptide (e.g., K)-hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., growth factor or GF-targeting peptide)-KKAAVV(K)(SEQ ID NO: 4)-hydrophobic tail (e.g., comprising an alkyl chain of 8-24 carbons). In some embodiments, the hydrophobic tail is attached to the (K) sidechain.

In some embodiments, provided herein are nanofibers and nanostructures assembled from the peptide amphiphiles described herein. In some embodiments, a nanofiber is prepared by the self-assembly of the PAs described herein. In some embodiments, a nanofiber comprises or consists of PAs displaying a growth factor or GF-targeting peptide peptide. In some embodiments, the growth factor or GF-targeting peptide peptides are displayed on the surface of the nanofiber. In some embodiments, in addition to PAs displaying TF-targeting peptides, filler PAs are included in the nanofibers. In some embodiments, filler PAs are peptide amphiphiles, as described herein (e.g., structural segment, charged segment, hydrophobic segment, etc.), but lacking a bioactive moiety. In some embodiments, the filler PAs and growth factor PAs or GF-targeting PAs self-assemble into a nanofiber comprising both types of PAs. In some embodiments, nanostructures (e.g., nanofibers) assembled from the peptide amphiphiles described herein are provided.

In some embodiments, PA nanofibers and/or solutions comprising PA nanofibers provide a scaffold and/or environment for supporting growth factors (or other bioactive agents), but are not covalently linked to such growth factors (or other bioactive agents).

In some embodiments, nanostructures are assembled from (1) PAs bearing a bioactive moiety (e.g., growth factor or GF-targeting peptide) and (2) filler PAs (e.g., PAs not-labeled or not displaying a bioactive moiety, etc.). In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) PAs bearing a bioactive moiety (e.g., growth factor or GF-targeting peptide moiety). In some embodiments, nanostructures (e.g., nanofibers) comprise and at least 2% (e.g., 2%, 3%, 4%, 5%, 10%, 15%, 20%, 25%, 30%, 35%, 40%, 45%, 50%, 55%, 60%, 65%, 70%, 75%, 80%, 85%, 90%, 95%, 98%, or any ranges there between) PAs bearing a bioactive moiety (e.g., growth factor or GF-targeting peptide moiety). In some embodiments, nanofibers comprise at least 50% (e.g., 50%, 55%, 60%, 65%, 70%, 75%, 80%, 85%, 90%, 95%, 98%, or any ranges there between) filler peptide amphiphiles. In some embodiments, the ratio of PAs bearing a bioactive moiety to filler PAs determines the density of bioactive moieties (e.g., growth factor or GF-targeting moiety) displayed on the nanostructure surface.

In some embodiments, the materials described herein find use in the delivery of growth factors or other bioactive agents for the repair of tissue/bone defects and/or regeneration of tissue/bone. Suitable agents for use in embodiments herein include bone morphogenic proteins (e.g., BMP-1, BMP-2, BMP-4, BMP-6, and BMP-7); members of the transforming growth factor beta (TGF-β) superfamily including, but not limited to, TGF-β1, TGF-β2, and TGF-β3; growth differentiation factors (GDF1, GDF2, GDF3, GDF5, GDF6, GDF7, myostatin/GDF8, GDF9, GDF10, GDF11, and GDF15); vascular endothelial growth factor (VEGF); fibroblast growth factor (FGF); etc. These agent, or others, may be covalently linked to PAs, non-covalently associated with peptides displayed on PA nanofibers, embedded within a PA nanofiber matrix, embedded within the composite compositions described herein, etc.

Compositions and methods herein find use in a variety of applications. As a bone-void filler, the paste-like consistency of the PA/polymer mixtures allows surgeons to easily adapt the material into any size bone defect, then after implantation the nanofibers cause the paste to gel in the shape of the bone defect. This material induces bone growth, and it can be used to deliver growth factors into the defect site that will be released over time from the nanofiber gel. Cranial and spinal bone regeneration and repair are particular applications. Bone repair is a critical concern for surgical procedures that remove part of the bone from the skull to expose the brain (craniotomies) and cranial injuries. Bone resorption (process by which bone cells break down bone and release the mineral from the bone) and nonunion of the skull defects are addressed by the compositions and methods herein.

Embodiments herein also find use in facilitating cartilage regenerations. Cartilage is affected by various diseases including congenital morphological anomalies such as cleft lip and palate, trauma to joint, large deficits after surgery for tumors or cancers, ageing-related diseases such as osteoarthritis, and inflammatory diseases such as rheumatoid arthritis. Once the cartilage tissues are damaged due to those disorders, it becomes difficult to maintain the morphology of face or body, as well as resulting in deterioration of daily activities. Cartilage tissues have limited capacity for self-repair. Cartilage diseases have traditionally been treated with transplantation of the autologous cartilage, or replacement with artificial joints; there are issues with those types of treatment, such as durability, infection, and invasiveness of donor sites. For cartilage regeneration, the compositions localize and maintain cells and growth factors within the defect site. In some embodiments, the compositions herein are implanted through minimally invasive means and biodegrade into amino acids and lipids that are safely cleared by the body.

EXPERIMENTAL

Example 1

Rat Model

Experiments were conducted during development of embodiments herein to evaluate the effectiveness of the compositions described herein in vivo, in a rat model (FIG. 1A). In Vivo experiments were performed using the Nano-Slurry as a delivery vehicle from the BMP2 growth factor in a spinal fusion model performed on rats.

Materials and Methods

Synthesis and Purification

The PA molecules used for this study, TSPHVPYGGGS-E3A3V3-$C_{16}$ (BMP2-PA) (SEQ ID NO: 5) and E3A3V3-$C_{16}$ (Diluent PA) (SEQ ID NO: 6), were synthesized by standard solid-phase Fmoc chemistry on a CS Bio automated peptide synthesizer using previously reported methods (Lee et. al. Advanced Healthcare Materials 4(1), (2015) 131-141; incorporated by reference in its entirety). The resulting product was purified using standard reversed-phase high performance liquid chromatography. The purity and accurate mass for each PA was verified using liquid chromatography/mass spectrometry on an electrospray ionization quadruple time-of-flight mass spectrometer. PA molecules were then sterile-filtered, aliquoted, lyophilized, and stored at −80° C. prior to use.

Implant Material Preparation

All PA solutions were solubilized in sterile MilliQ water. On the day of surgery, the PA solution was mixed with stock rhBMP-2 solution (1,500 μg/mL) and water to achieve the desired final concentration of rhBMP-2 dispersed in the PA nanofiber solution. For the NanoSlurry preparation, the nanofiber solution prepared above was mixed with dry collagen particles to form a paste. After mixing in the specified rhBMP-2 concentration, 130 uL of the NanoSlurry mixture was loaded into a sterile 1 mL syringe.

Group 1, n=8
Formulation:
absorbable collagen sponge (ACS) with 0.1 ug r-BMP-2
  1) Load into 130 uL of 0.38 ug rBMP-2/mL onto 4 mm×10 mm ACS sheet Group 2, n=12
Formulation:
5 wt % absorbable collagen sponge (ACS) particles, (0.1 ug rBMP-2/animal) 0.38 ug rBMP-2/mL
  1) Mix 1.5 mL of water with 167 uL of 4.04 ug rBMP-2/mL,
  2) Mix with 87.7 mg of ground up ACS. (total volume assumed to be 1.7547 mL
  3) Load into 130 uL into 1 cc syringes for implantation into one defect X10

Group 3, n=12
Formulation:
5 wt % absorbable collagen sponge (ACS), 1 wt % PA, (0.1 ug rBMP-2/animal) 0.38 ug rBMP-2/mL
1) Mix 1.5 mL of 1.11 wt % E3 with 167 uL of 4.04 ug rBMP-2/mL,
2) Mix with 87.7 mg of ground up ACS. (total volume assumed to be 1.7547 mL
3) Load into 130 uL into 1 cc syringes for implantation into one defect X10

Rat Posterolateral Lumbar Intertransverse Spinal Fusion

Experiments conducted during development of embodiments herein were approved by the Institutional Animal Care and Use Committee and was conducted in line with IACUC policies and procedures. Animals were first assigned to one of three treatment groups: group 1: 100 ng BMP2 with absorbable collagen sponge (ACS), group 2: 100 ng BMP2 with collagen particles, group 3: 100 ng BMP2 with NanoSlurry. Surgical Procedures: Rats were maintained on a heating pad under continuous anesthesia with an isoflurane inhalational anesthetic delivery system, and they were monitored by an assistant for cardiac or respiratory difficulties throughout the procedure. Utilizing a previously-described surgical technique, a posterior midline incision was made over the lumbar spinous processes, after which two separate fascial incisions were made 4 mm from the midline. The L4 and L5 transverse processes were exposed using a muscle-splitting approach via blunt dissection down to the periosteum. After adequate exposure, the fusion bed was irrigated with sterile gentamicin/saline solution, and a high-speed burr was used to decorticate the superficial cortical layer of the transverse processes. Graft materials were then implanted bilaterally in the paraspinal musculature between the transverse processes. The fascia and skin incisions were closed using a simple interrupted pattern with a 3-0 Monocryl absorbable suture, which was removed from the skin 7-10 d post-surgery. Following surgery, rats were housed in separate cages and allowed to eat, drink, and bear weight ad libitum.

Manual Palpation

Fusion was assessed via manual palpation following euthanasia at 8 weeks post-surgery. Spines were scored by three blinded observers using a previously established scoring system: 0=no bridging; 1=unilateral bridging; 2=bilateral bridging; and 3=bilateral bridging with abundant bone. Spines that received an average score of 1.0 or greater were considered successfully fused.

Results

Figure 1B:
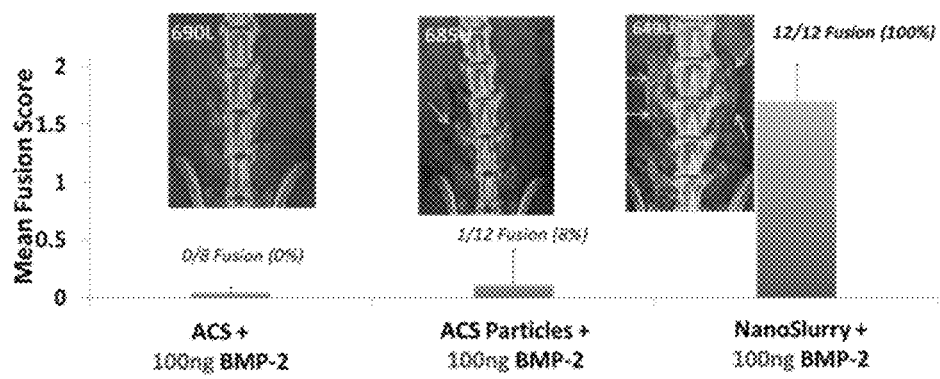

Results of the rat study are depicted in FIG. 1B. Group 3 resulted in 100% fusion for all animals. These results demonstrate to effectiveness of the NanoSlurry as a growth factor delivery vehicle. The two control groups, group 1 and 2, contained only collagen and water, and these groups did not produce significant spinal fusion measure by manual palpation. These results show that the nanofibers contained within the NanoSlurry formulation are responsible for the effective delivery of rhBMP-2 and the resulting spinal fusion.

Example 2

Rabbit Posterolateral Spinal Fusion

Figure 2:
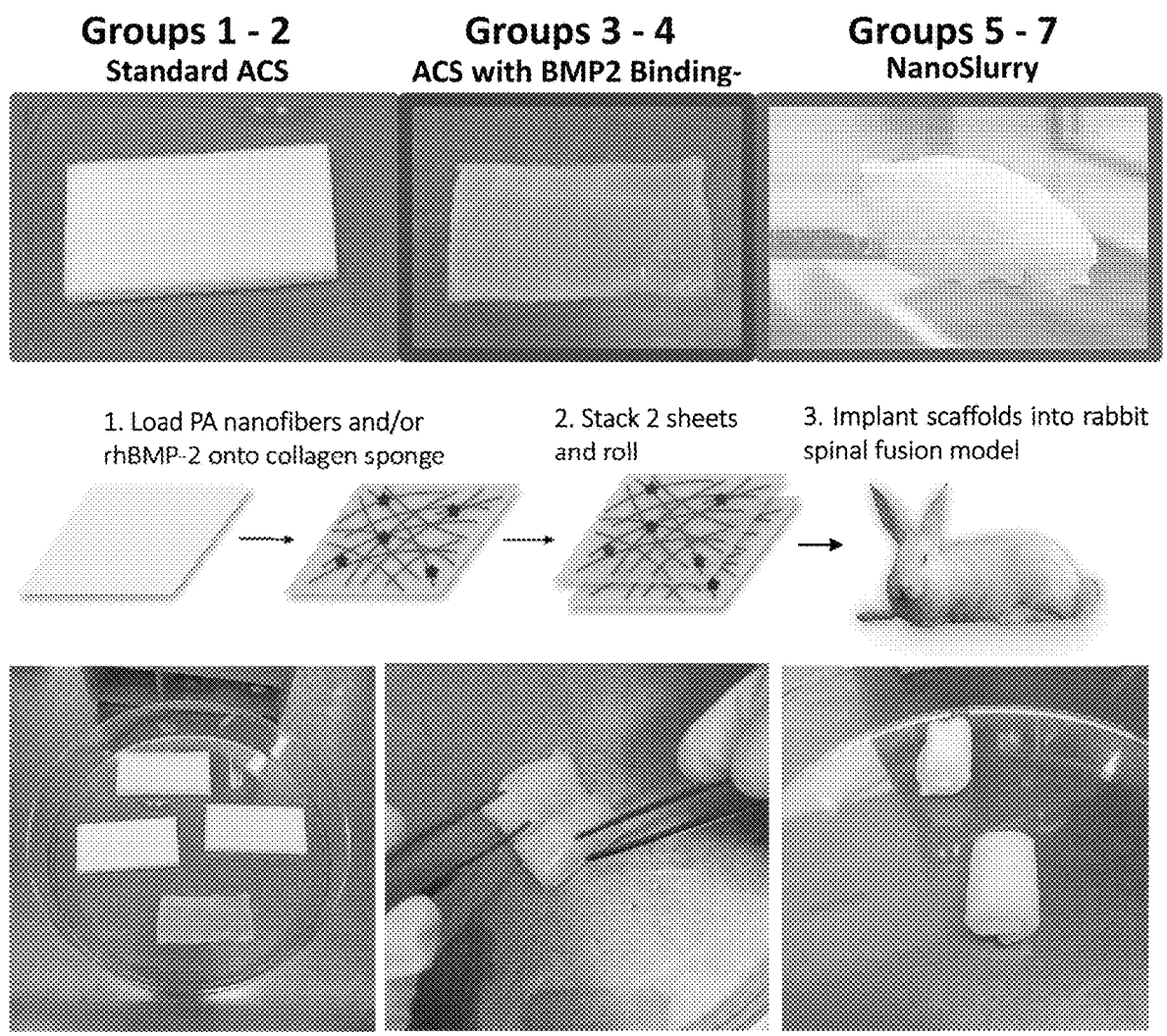
FIG. 2. Experimental procedure and treatment groups for the rabbit posterolateral spinal fusion model. Implants from groups 1-4 were prepared using the soak-and-roll technique. The NanoSlurry groups (5-7) were applied to the fusion bed directly from 5 mL syringes.

Experiments were conducted in a rabbit posterolateral spinal fusion model during development of embodiments herein to evaluate the effectiveness of the compositions described herein in vivo (FIG. 2).

Materials and Methods
Synthesis and Purification

The PA molecules used for this study, TSPHVPYGGGS-E3A3V3-$C_{16}$ (BMP2-PA) (SEQ ID NO: 5) and E3A3V3-$C_{16}$ (Diluent PA) (SEQ ID NO: 6), were synthesized by standard solid-phase Fmoc chemistry on a CS Bio automated peptide synthesizer using previously reported methods (Lee et. al.). The resulting product was purified using standard reversed-phase high performance liquid chromatography. The purity and accurate mass for each PA was verified using liquid chromatography/mass spectrometry on an electrospray ionization quadruple time-of-flight mass spectrometer. PA molecules were then sterile-filtered, aliquoted, lyophilized, and stored at −80° C. prior to use.

Implant Material Preparation

All PA solutions were solubilized in sterile MilliQ water. On the day of surgery, the PA solution was mixed with stock rhBMP-2 solution (1,500 µg/mL) and water to achieve the desired final concentration of rhBMP-2 dispersed in the PA nanofiber solution. The PA/rhBMP-2 solution was then soaked onto an ACS scaffold, stacked in pairs, then rolled into the final implant (FIG. 2).

For the NanoSlurry preparation, the nanofiber solution prepared above was not added to a collagen sponge, but instead, it was mixed with dry collagen particles to form a paste. After mixing in the specified rhBMP-2 concentration, 2 mL of the NanoSlurry mixture was loaded into a sterile 5 mL syringe.

Preoperative Animal Care

Twenty-four hours prior to surgery, animals were placed in a collar and received a fentanyl patch (12 µg/hr) on the inside of the right ear pinna.

Surgical Site Preparation

The surgical site was shaved and prepped in a sterile fashion using a Betadine (povidone-iodine) scrub and alcohol swab protocol.

Surgical Procedure

Rabbits were anesthetized using a ketamine/xylazine cocktail injection, and sedation was maintained using 2.5% inhalation isoflurane delivered via nose cone. The surgical site was sterilely draped. Using manual palpation to identify the iliac crests, the locations of L3-L6 vertebral bodies were approximated, and local anesthesia was applied subcutaneously at the incision site. A 10-cm midline incision was made along the dorsal lumbar region directly over the corresponding spinous processes. To expose the L4-L5 transverse processes, bilateral longitudinal fascial and muscle incisions were made lateral to the L4 and L5 spinous processes (lateral to the facet joints). Paraspinal musculature was separated from the vertebral bodies and transverse processes using a combination of blunt and sharp dissection.

Intertransverse gutters spanning L4-L5 were created. Once the transverse processes were adequately exposed, 0.5 ml gentamicin solution was applied into each gutter. Shortly after application, excess gentamicin solution was removed with sterile gauze. An electric burr was then used to decorticate the cortical layers of the L4 and L5 transverse processes. After complete decortication, implants spanning the L4-L5 transverse processes were placed bilaterally into the surgical beds. The fascial layer was then closed using a figure-8 stitch with a 3-0 absorbable suture. Subcutaneous tissue was reapposed using subdermal buried 3-0 absorbable sutures in an interrupted fashion. Skin was closed with wound clips.

Animals were recovered by veterinary staff, including post-operative analgesia and fluid replacement. All animals received 3 days of prophylactic post-operative antibiotic treatment and nonsteroidal anti-inflammatory medications for discomfort.

X-Rays

Radiographs were taken at 2-week intervals until sacrifice at 8 weeks post-operative in the CCM facilities. For radiography, rabbits were physically immobilized using the Lomir bunny swaddle, which is a snuggle device that holds the animals in sternal positioning to facilitate imaging of the lumbar spine without the need for anesthesia.

Palpation and Fusion Assessment

Animals were euthanized 8 weeks post-operative, and spines were harvested for evaluation of fusion via manual palpation, which was performed by three independent, blinded observers using a graded scoring system as we have previously described (0, no bridging bone; 1, fusion unilaterally with evidence of L4-L5 bridging bone; 2, bilateral bridging bone). Individual scores for each specimen were then averaged. An average score of ≥1.0 was considered solidly fused.

Results

Figure 3:
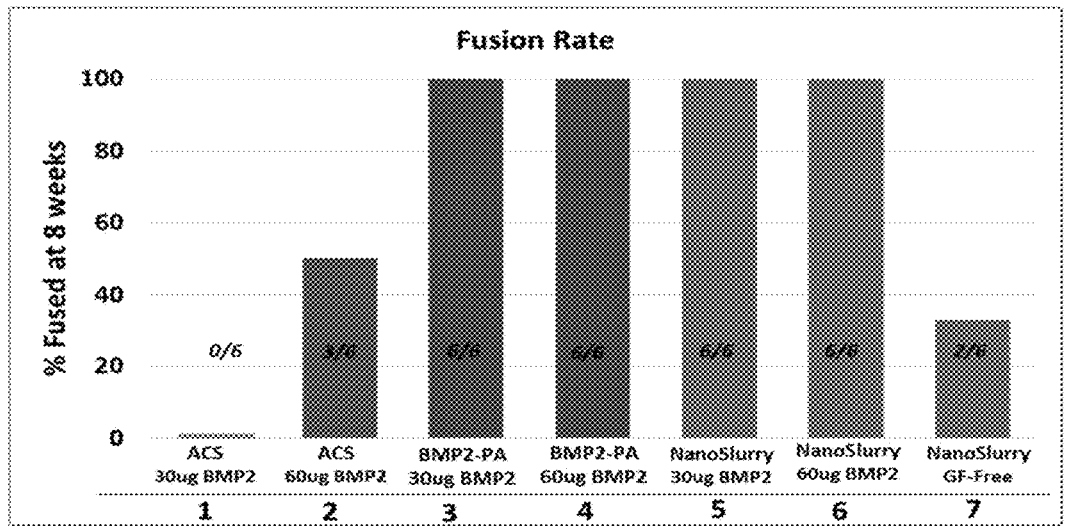
FIG. 3. Fusion rates and scores for the rabbit posterolateral spinal fusion model based on blinded manual palpation.
Figure 3:
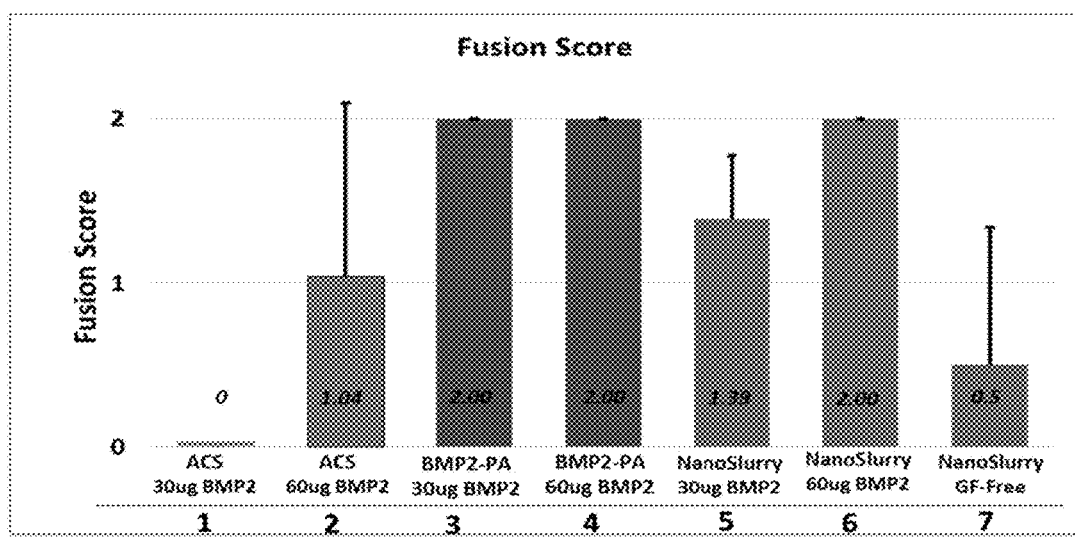
Figure 4:
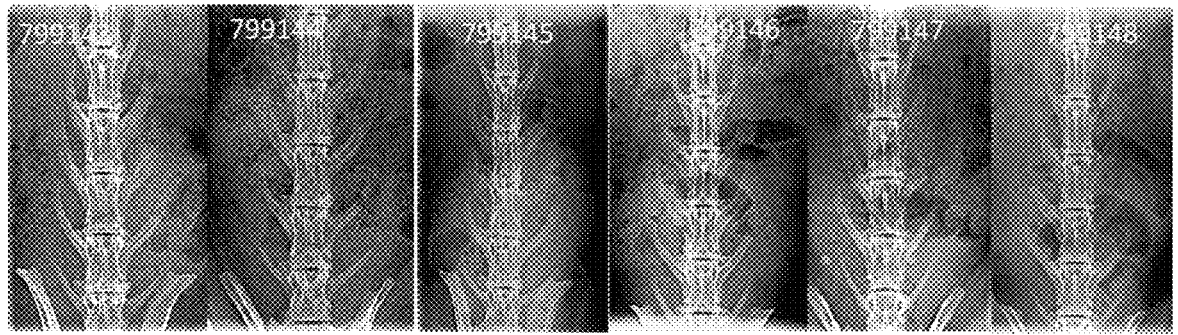
FIG. 4. All X-rays at final time point eight weeks post implant for the rabbit posterolateral spinal fusion model.
Figure 4:
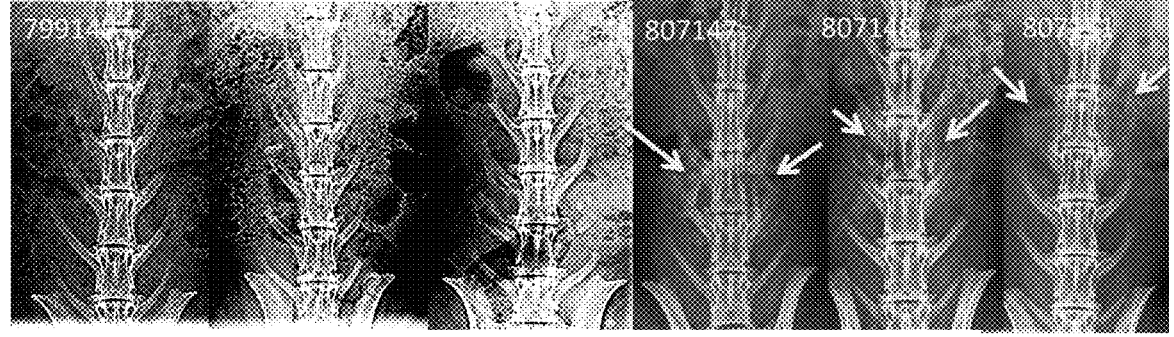
Figure 4:
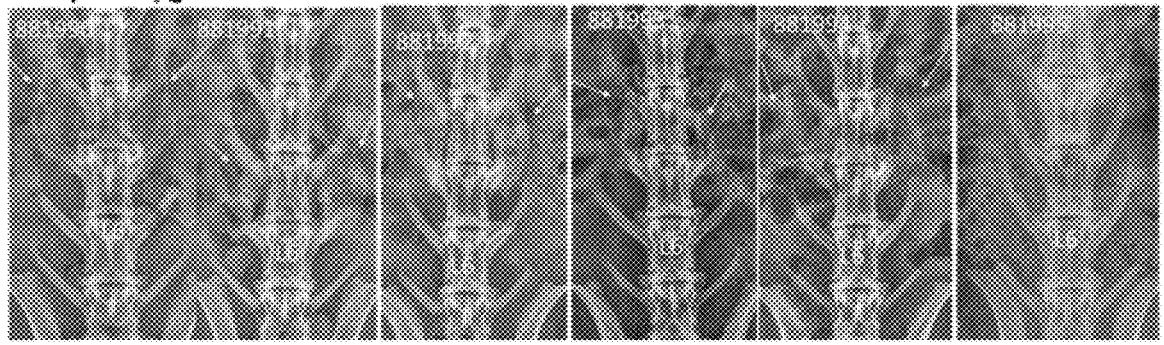
Figure 4:
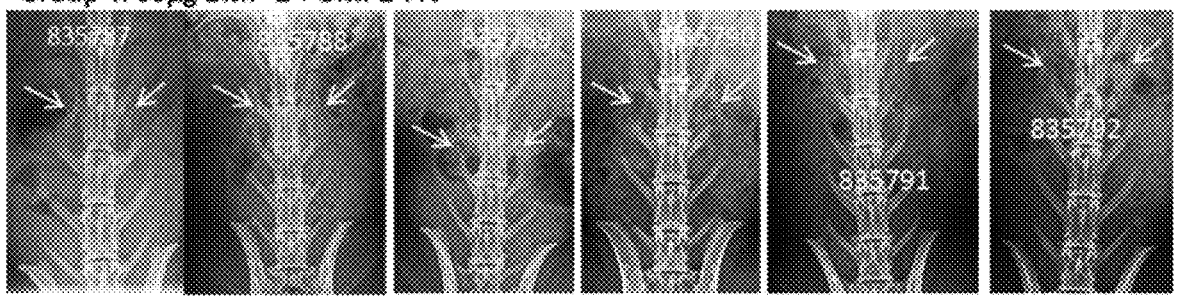
Figure 4:
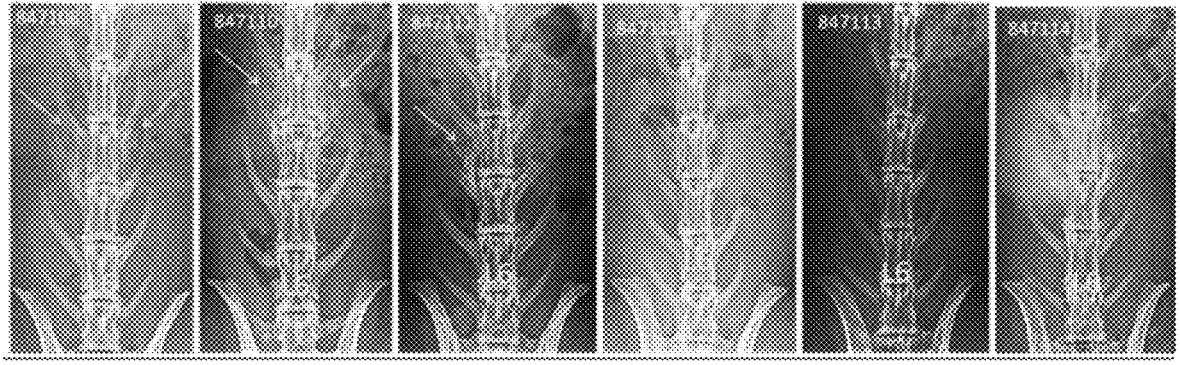
Figure 4:
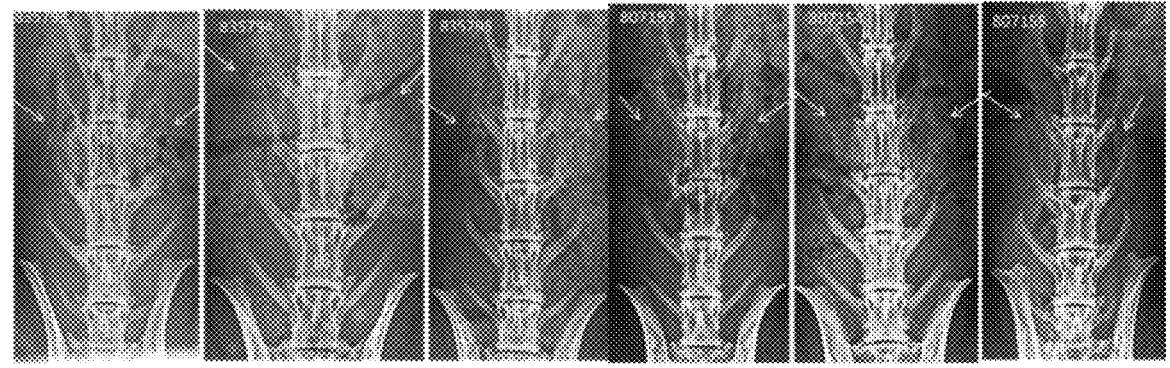
Figure 4:
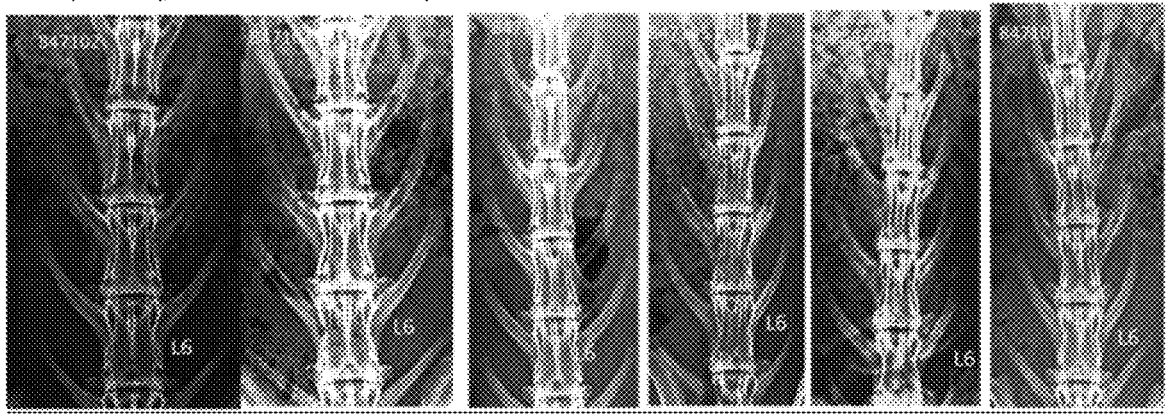
Figure 5:
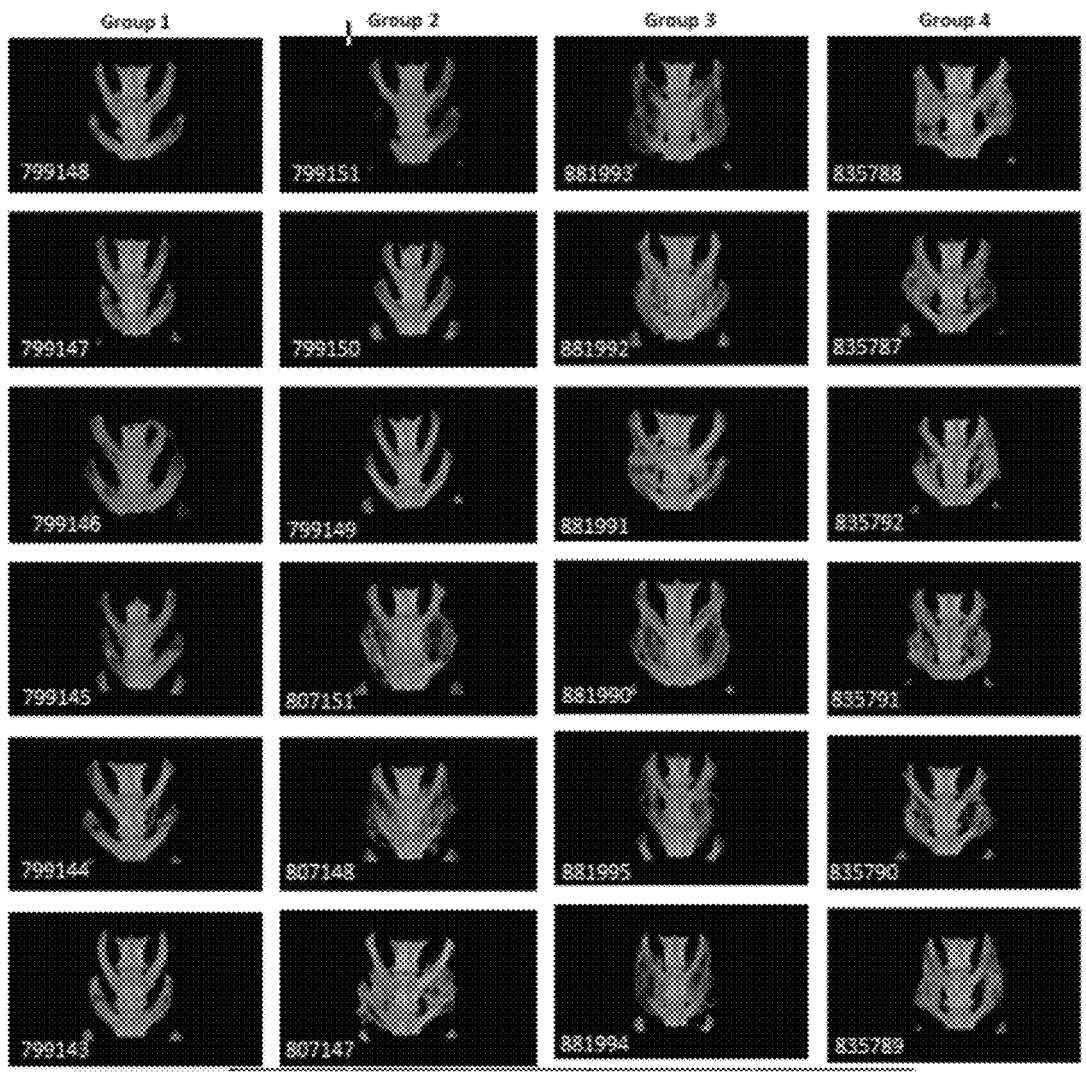
FIG. 5. Rabbit posterolateral spinal fusion model; uCT images from selected groups, 8 weeks post operation.
Figure 6:
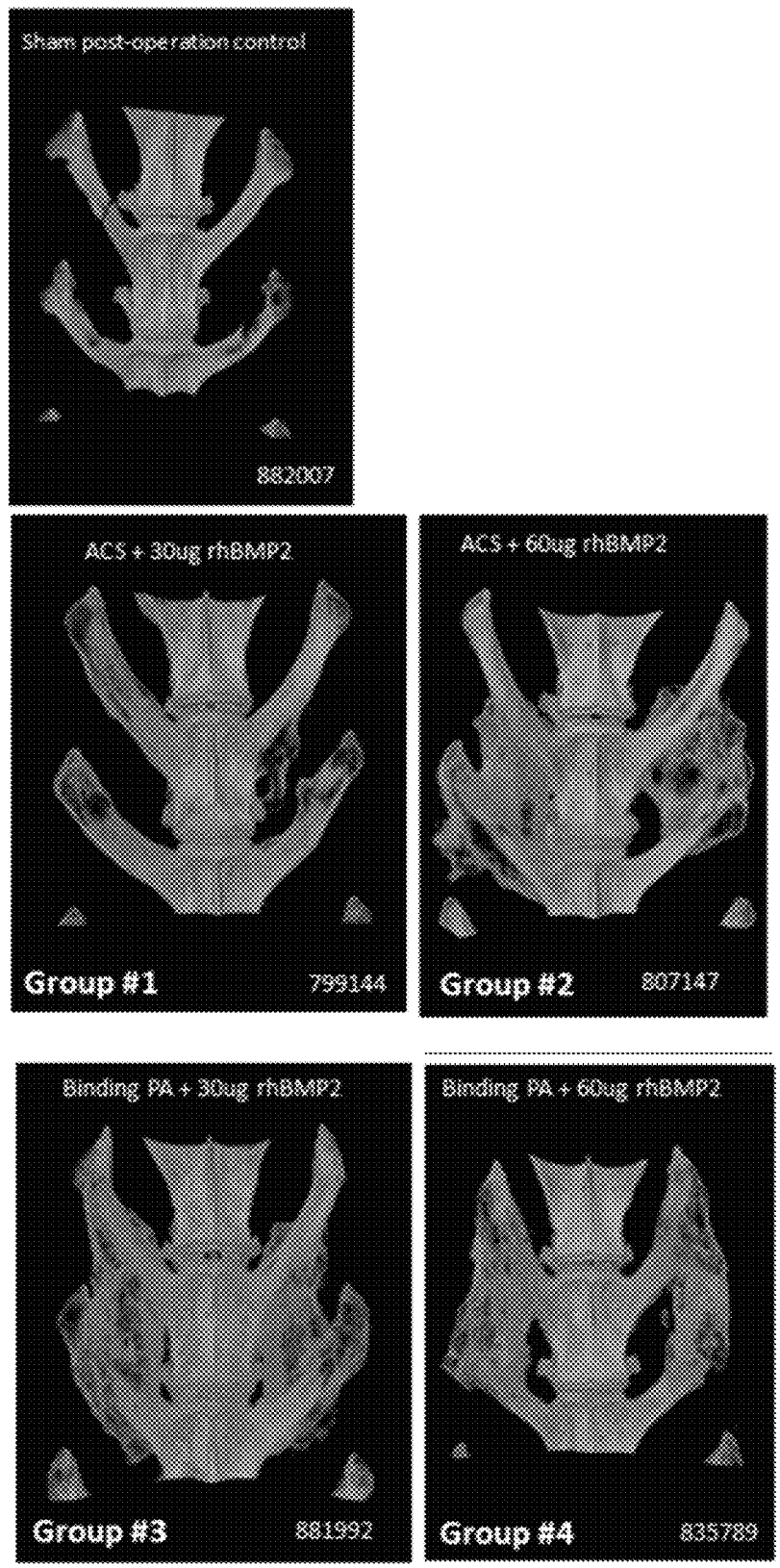
FIG. 6. Rabbit posterolateral spinal fusion model; uCT images showing individuals with the greatest amount of bone growth from each of the selected groups. "Sham post-operation control" representative was euthanized immediately following the PLF decortication procedure.

The two control groups (groups 1 and 2, ACS+30 and 60 μg rhBMP-2, respectively) achieved fusion rates of 0% and 50% respectively, as expected (FIG. 3). We found that rhBMP-2 delivery was enhanced with the addition of PA nanofibers (group 3 and 4). The addition of PA to the implant resulted in 100% fusion rates and the highest possible fusion score in all animals (bilateral fusion in all animals) when delivering either 30 ug or 60 ug of rhBMP-2. We believe these impressive results are due to rhBMP-2 retention by the PA nanogel, avoiding a burst release of rhBMP-2, and instead allowing for slower growth factor release kinetics. PA nanofibers bind strongly to the rhBMP-2, preventing a burst release, but they also provide a barrier to enzymes and other biological factors that could otherwise de-activate the rhBMP-2. We hypothesize that the PA nanogels protect and retain most of the rhBMP-2 within the nanofiber matrix until infiltrating cells degrade the nanofiber matrix and gain access to the retained growth factor.

During this study, we developed and tested a new method for applying the PA nanofibers for spinal fusion, termed NanoSlurry. The rationale behind the NanoSlurry design was to allow surgeons an easier way to apply the PA nanofibers into a fusion site that could mold and form into arbitrary spaces. The NanoSlurry contains a comparable amount of collagen material as the previous groups (1-4) and contained no new materials. The NanoSlurry groups also resulted in a 100% fusion rate when delivering either 30 ug or 60 ug of rhBMP-2.

Interestingly, based on manual palpation, the NanoSlurry elicited a measurable amount of fusion in two of the six animals without the addition of rhBMP-2. This result mirrors our previous findings in the rat PLF spinal fusion model.[1] We plan to send these two specimens out for non-decal histology in order to visualize the mineralizing tissue bridging those transverse processes. Nonetheless, we believe that the osteogenic properties in this group arise from the material's ability to both bind and retain endogenous growth factors while offering a conductive scaffold for infiltrating cells.

Experiments conducted using the rabbit posterolateral spinal fusion model demonstrate that PA nanofiber gels provide of powerful delivery vehicle for rhBMP-2 that outperforms the "ACS only" delivery method (100% fusion rate with Nanofiber gels vs 50% with ACS). PA nanogel delivery of rhBMP-2 at the 60 μg/animal and 30 μg/animal dose resulted in 100% fusion; it is contemplated that lower doses will achieve similarly robust fusion.

What is claimed is:

1. An osteoconductive composite material comprising: (1) peptide amphiphile nanofibers displaying a BMP-2 binding peptide, (2) biocompatible polymer microparticles of porous absorbable collagen sponge material, and (3) bone morphogenic protein 2 (BMP-2).

2. The composite material of claim 1, wherein the peptide amphiphile nanofibers are derived from a peptide amphiphile solution.

3. The composite material of claim 1, wherein the peptide amphiphile nanofibers comprise a bioactive peptide amphiphile comprising a hydrophobic segment, a structural segment, a charged segment, and the BMP-2 binding peptide.

4. The composite material of claim 3, wherein the peptide amphiphile nanofibers further comprise a filler peptide amphiphile comprising a hydrophobic segment, a structural segment, and a charged segment.

5. A method of promoting repair of a bone or cartilage defect comprising administering the composite material of claim 1 to the bone or cartilage defect.

6. A method of preparing a composite material of claim 1, the method comprising:

(a) combining a the peptide amphiphiles displaying a BMP-2 binding peptide with the BMP-2 in an aqueous solution; and (b) mixing the biocompatible polymer microparticles of porous absorbable collagen sponge material into the aqueous solution.

7. The method of claim 6, wherein the microparticles are produced by grinding and/or lyophilizing an absorbable collagen sponge.

* * * * *